US008135545B2

(12) United States Patent
Sproles (10) Patent No.: US 8,135,545 B2
(45) Date of Patent: Mar. 13, 2012

(54) SYSTEM AND METHOD FOR COLLECTING DATA REGARDING BROAD-BASED NEUROTOXIN-RELATED GENE MUTATION ASSOCIATION

(75) Inventor: Dean Iverson Sproles, Seattle, WA (US)

(73) Assignee: Iverson Genetic Diagnostics, Inc., Bothell, WA (US)

( * ) Notice: Subject to any disclaimer, the term of this patent is extended or adjusted under 35 U.S.C. 154(b) by 1048 days.

(21) Appl. No.: 11/938,161

(22) Filed: Nov. 9, 2007

(65) Prior Publication Data

US 2009/0125551 A1    May 14, 2009

(51) Int. Cl.
*G01N 33/48* (2006.01)
*C12Q 1/68* (2006.01)
*G06G 7/58* (2006.01)
*G06F 7/60* (2006.01)

(52) U.S. Cl. .............. 702/19; 435/6; 702/20; 703/2; 703/11; 700/90

(58) Field of Classification Search ............... None
See application file for complete search history.

(56) References Cited

U.S. PATENT DOCUMENTS

| 6,017,496 | A | 1/2000 | Nova et al. |
| 6,410,229 | B1 | 6/2002 | Lockhart et al. |
| 6,656,691 | B2 | 12/2003 | Begovich et al. |
| 6,660,474 | B1 | 12/2003 | Feder et al. |
| 2007/0042369 | A1 | 2/2007 | Reese et al. ............... 435/6 |

FOREIGN PATENT DOCUMENTS

| WO | WO 03/017038 A2 | 2/2003 |
| WO | WO 2006/116622 A2 | 11/2006 |

OTHER PUBLICATIONS

Achiron et al., "Blood transcriptional signatures of multiple sclerosis: unique gene expression of disease activity", *Ann. Neurol.*, 55:410-417 (2004).
Augen, J., "Targeting the transcriptome", *Modern Drug Discovery*, 7(4):39-44 (2004).
Brentany et al., "The generation and utilization of a cancer-oriented representation of the human transcriptome by using expressed sequence tags", *Proc. Natl. Acad. Sci. USA*, 100(23):13418-13423 (2003).
Desany et al., "Bioinformatics and cancer target discovery", *Drug Discovery Today*, 9(18):795-802 (2004).
Lewis et al., "Bioinformatics—the mammalian gene mutation database", *Mutagenesis*, 15(5):411-414 (2000).
Waters et al., "Toxicogenomics and systems toxicology: aims and prospects", *Nat. Rev. Gen.*, 5:936-948 (2004).
International Search Report for PCT/US2007/069931.
Written Opinion of the International Searching Authority for PCT/US2007/069931.

*Primary Examiner* — Shubo Zhou
(74) *Attorney, Agent, or Firm* — Kevin D. Jablonski; Graybeal Jackson LLP (57) ABSTRACT

Broad-based genetic mutation association gene transcript test and data structure. Genetic mutation considerations for this unique test include a custom set of genetic sequences associated in peer-reviewed literature with various known genetic mutation related to exposure to toxic substances. Such genetic mutations include specific gene sequence alterations based on exposure to diesel fuel, aviation fuel, jet fuel, and many other toxic substances often needed in the aviation and refining industries. The base dataset may be developed through clinical samples obtained by third-parties. Online access of real-time phenotype/genotype associative testing for physicians and patients may be promoted through an analysis of a customized microarray testing service.

19 Claims, 7 Drawing Sheets

| TEST | ID | POLYMORPHISM | EXPRESSION RATE | DISCUSSION |
|---|---|---|---|---|
| CBS | UIA03 | C | 80.0% | T variation results in lower post methionine load plasma homocysteine levels when compared to individuals with the C/C genotype. T variation has been associated with decreased risk of coronary artery disease and increased responsiveness to the plasma homocysteine lowering effects of folic acid.<br>PUBMED ID#10833331 |
| COMT<br>↑<br>510 | UIA04<br>↑<br>511 | G<br>↑<br>512 | 514<br>90.0%<br>↑<br>513 | The methylation of dopamine by COMT is an important mechanism for dopamine inactivation and dopaminergic tone in the CNS. The G > A transition at position 472 (valine > methionine) influence protein expression and enzyme activity in an allelic dose/response manner. The val allele is associated with thermostability and high activity val allele showed poorer attentional control and performance on tests of executive cognition associated with inefficient precortical activity. The met allele encodes the low activity variant and is associated with better performance on tests of prefrontally mediated cognition The GG genotype was present in 29% of autistic cases and 20% of unaffected controls and was associated with a 1.74 fold increased susceptibility to autism.<br>PUBMED ID# 16917939 |

SYSTEM AND METHOD FOR COLLECTING DATA REGARDING BROAD-BASED NEUROTOXIN-RELATED GENE MUTATION ASSOCIATION

CROSS-REFERENCE TO RELATED PATENT APPLICATION

This patent application is related to the patent application entitled "BROAD-BASED NEUROTOXIN-RELATED GENE MUTATION ASSOCIATION FROM A GENE TRANSCRIPT TEST" filed concurrently with this application on Nov. 9, 2007 and having U.S. patent application Ser. No. 11/938,029.

BACKGROUND

A neurotoxin is a toxic substance that acts specifically on nerve cells and cause at least some level of neurotoxicity in living organisms, i.e., altering the normal functions of the nervous system. Such neurotoxins typically interact with membrane proteins and ion channels when an organism inhales, ingests or otherwise comes into contact with these reactive agents. Common examples of neurotoxins occur in nature in the venom of bees, scorpions, pufferfish, spiders and snakes, all of which may contain many different toxins. Such neurotoxins are typically injected from a sting or a bite and often affect the central nervous system leading to paralysis or other neural damage, Another set of examples of common neurotoxins include toxins that may be inhaled or ingested from gasoline, aviation fuel, paint thinner, alcohol and the like. Toxins ingested from the environment are described as exogenous and include gases (such as carbon monoxide), metals (such as mercury), liquids (ethanol) and an endless list of solids. When exogenous toxins are ingested, the effect on neurons is largely dependent on dosage. Thus, ethanol (alcohol) is inebriating in low doses, only producing mild neurotoxicity.

Neurotoxicity occurs when the exposure to natural or man-made toxic substances alters the normal activity of the nervous system. This can eventually disrupt or even kill neurons, key cells that transmit and process signals in the brain and other parts of the nervous system. Neurotoxicity can result from exposure to substances used in chemotherapy, radiation treatment, drug therapies and organ transplants, as well as exposure to heavy metals such as lead and mercury, certain foods and food additives, pesticides, industrial and/or cleaning solvents, cosmetics, and some naturally occurring substances. Symptoms may appear immediately after exposure or be delayed. They may include limb weakness or numbness, loss of memory, vision, and/or intellect, headache, cognitive and behavioral problems and sexual dysfunction. Individuals with certain disorders may be especially vulnerable to neurotoxins.

The term neurotoxic is used to describe a substance, condition or state that damages the nervous system and/or brain, usually by killing neurons. The term is generally used to describe a condition or substance that has been shown to result in observable physical damage. The presence of neurocognitive deficits alone is not usually considered sufficient evidence of neurotoxicity, as many substances exist which may impair neurocognitive performance without resulting in the death of neurons. This may be due to the direct action of the substance, with the impairment and neurocognitive deficits being temporary, and resolving when the substance is metabolized from the body. In some cases the level or exposure-time may be critical, with some substances only becoming neurotoxic in certain doses or time periods. If exposure to neurotoxins is prolonged or acute, a person may experience a mutation on a genetic level such that his or her DNA and/or RNA changes.

Genetic disorders afflict many people and remain the subject of much study and misunderstanding. Typical genetic disorders occur when specific gene sequences are not maintained as expected, such as with Multiple Sclerosis and Type II diabetes. Currently, around 4,000 genetic disorders are known, with more being discovered as more is understood about the human genome. Most disorders are quite rare and affect one person in every several thousands or millions while other are more common such as cystic fibrosis wherein about 5% of the population of the United States carry at least one copy of the defective gene.

A person's genetic makeup is reflected through Deoxyribonucleic Acids (DNA). DNA is a molecule that comprises sequences of nucleic acids (i.e., nucleotides) that form the code which contains the genetic instructions for the development and functioning of living organisms. A DNA sequence or genetic sequence is a succession of any of four specific nucleic acids representing the primary structure of a real or hypothetical DNA molecule or strand, with the capacity to carry information. As is well understood in the art, the possible nucleic acids (letters) are A, C, G, and T, representing the four nucleotide subunits of a DNA strand—adenine, cytosine, guanine, and thymine bases covalently linked to phospho-backbone. Typically the sequences are printed abutting one another without gaps, as in the sequence AAAGTCTG. A succession of any number of nucleotides greater than four may be called a sequence.

Ribonucleic acid (RNA) is a nucleic acid polymer consisting of nucleotide monomers, that acts as a messenger between DNA and ribosomes, and that is also responsible for making proteins by coding for amino acids. RNA polynucleotides contain ribose sugars unlike DNA, which contains deoxyribose. RNA is transcribed (synthesized) from DNA by enzymes called RNA polymerases and further processed by other enzymes. RNA serves as the template for translation of genes into proteins, transferring amino acids to the ribosome to form proteins, and also translating the transcript into proteins.

A gene is a segment of nucleic acid that contains the information necessary to produce a functional product, usually a protein. Genes contain regulatory regions dictating under what conditions the product is produced, transcribed regions dictating the structure of the product, and/or other functional sequence regions. Genes interact with each other to influence physical development and behavior. Genes consist of a long strand of DNA (RNA in some viruses) that contains a promoter, which controls the activity of a gene, and a coding sequence, which determines what the gene produces. When a gene is active, the coding sequence is copied in a process called transcription, producing an RNA copy of the gene's information. This RNA can then direct the synthesis of proteins via the genetic code. However, RNAs can also be used directly, for example as part of the ribosome. These molecules resulting from gene expression, whether RNA or protein, are known as gene products.

The total complement of genes in an organism or cell is known as its genome. The genome size of an organism is loosely dependent on its complexity. The number of genes in the human genome is estimated to be just under 3 billion base pairs and about 30,000 genes.

As previously mentioned, certain genetic mutations and/or disorders may result from DNA sequences being incorrectly coded. A Single Nucleotide Polymorphism or SNP (often time called a "snip") is a DNA sequence variation occurring when a single nucleotide—A, T, C, or G—in the genome (or other shared sequence) differs between members of a species (or between paired chromosomes in an individual). For example, two sequenced DNA fragments from different individuals, AAGCCTA to AAGCTTA, contain a difference in a single nucleotide. In this case, this situation may be referred to as having two alleles: C and T.

Within a population, Single Nucleotide Polymorphisms can be assigned a minor allele frequency—the ratio of chromosomes in the population carrying the less common variant to those with the more common variant. Usually one will want to refer to Single Nucleotide Polymorphisms with a minor allele frequency of ≧1% (or 0.5% etc.), rather than to "all Single Nucleotide Polymorphisms" (a set so large as to be unwieldy). It is important to note that there are variations between human populations, so a Single Nucleotide Polymorphism that is common enough for inclusion in one geographical or ethnic group may be much rarer in another.

Single Nucleotide Polymorphisms may fall within coding sequences of genes, noncoding regions of genes, or in the intergenic regions between genes. Single Nucleotide Polymorphisms within a coding sequence will not necessarily change the amino acid sequence of the protein that is produced, due to degeneracy of the genetic code. A Single Nucleotide Polymorphism in which both forms lead to the same polypeptide sequence is termed synonymous (sometimes called a silent mutation)—if a different polypeptide sequence is produced they are non-synonymous. Single Nucleotide Polymorphisms that are not in protein coding regions may still have consequences for gene splicing, transcription factor binding, or the sequence of non-coding RNA.

Variations in the DNA sequences of humans can affect how humans develop diseases, and/or respond to pathogens, chemicals, drugs, etc. However, one aspect of learning about DNA sequences that is of great importance in biomedical research is comparing regions of the genome between people (e.g., comparing DNA sequences from similar people, one with a genetic mutation and one without the genetic mutation). Technologies from Affymetrix™ and Illumina™ (for example) allow for genotyping hundreds of thousands of Single Nucleotide Polymorphisms for typically under $1,000.00 in a couple of days.

Microarray analysis techniques are typically used in interpreting the data generated from experiments on DNA, RNA, and protein microarrays, which allow researchers to investigate the expression state of a large number of genes—in many cases, an organism's entire genome—in a single experiment. Such experiments generate a very large volume of genetic data that can be difficult to analyze, especially in the absence of good gene annotation. Most microarray manufacturers, such as Affymetrix™, provide commercial data analysis software with microarray equipment such as plate readers.

Specialized software tools for statistical analysis to determine the extent of over- or under-expression of a gene in a microarray experiment relative to a reference state have also been developed to aid in identifying genes or gene sets associated with particular phenotypes. Such statistics packages typically offer the user information on the genes or gene sets of interest, including links to entries in databases such as NCBI's GenBank and curated databases such as Biocarta and Gene Ontology.

As a result of a statistical analysis, specific aspects of an organism may be genotyped. Genotyping refers to the process of determining the genotype of an individual with a biological assay. Current methods of doing this include Polymerase Chain Reaction (PCR), DNA sequencing, and hybridization to DNA microarrays or beads. The technology is intrinsic for test on father-/motherhood and in clinical research for the investigation of genetic mutation-associated genes.

Further, phenotyping is also a known process for assessing phenotypes. The phenotype of an individual organism is either its total physical appearance and constitution or a specific manifestation of a trait, such as size, eye color, or behavior that varies between individuals. Phenotype is determined to a large extent by genotype, or by the identity of the alleles that an individual carries at one or more positions on the chromosomes. Many phenotypes are determined by multiple genes and influenced by environmental factors. Thus, the identity of one or a few known alleles does not always enable prediction of the phenotype.

In a drawback of the current state of the art, the genotyping process is typically accomplished for a single patient or research sample in a single sampling for a single iteration and with a specific genetic mutation in mind for the genotyping. As such, the results are relatively isolated with respect to any possible comparison and analysis of other similarly situated patients. Furthermore, such isolation leads to inefficiencies in diagnostics and treatment of the underlying results of the test. Without a system for allowing the sharing of underlying data, all potential benefits of aggregating the data are lost. Thus, as genetic material samples are collected, they are done so from an individualistic approach without regard for benefits to be realized from aggregating the data from many genetic samples from many sample sources (i.e., people). What is needed is a broad-based genetic mutation association gene transcript test along with systems and methods associated therewith capable of allowing the assimilation of a wide range of data from a wide range of sources.

BRIEF DESCRIPTION OF THE DRAWINGS

The foregoing aspects and many of the attendant advantages of the claims will become more readily appreciated as the same become better understood by reference to the following detailed description, when taken in conjunction with the accompanying drawings, wherein:

DETAILED DESCRIPTION

The following discussion is presented to enable a person skilled in the art to make and use the subject matter disclosed herein. The general principles described herein may be applied to embodiments and applications other than those detailed above without departing from the spirit and scope of the present detailed description. The present disclosure is not intended to be limited to the embodiments shown, but is to be accorded the widest scope consistent with the principles and features disclosed or suggested herein.

The subject matter disclosed herein is related to transcriptional detection of single nucleotide polymorphisms (SNP) and insertion/deletion (I/D) genetic polymorphisms through a proportional analysis of RNA sequences detected through fluorescence hybridization on a custom manufactured microarray gene expression platform. SNPs may be identified through a specific design method (SNPs are typically assessed through DNA analysis). Considerations of genetic mutation due to exposure to neurotoxins for this unique test include a custom set of genetic sequences associated in peer-reviewed literature with various known genetic mutations caused by neurotoxins such as diesel fuel, aviation fuel (AvGas), petroleum refining gases, and others. The base dataset may be developed through clinical samples obtained by third-parties clinical groups, and in partial association with fuel refining industries. Online access of real-time phenotype/genotype associative testing for physicians and patients may be promoted through a testing service.

In biology, mutations are changes to the base pair sequence of genetic material (either DNA or RNA). Mutations can be caused by copying errors in the genetic material during cell division and by exposure to ultraviolet or ionizing radiation, chemical mutagens, or viruses. Such copying errors in a person may be classified as SNPs, insertions or deletions and may be detectable through an analysis of genetic material obtained from the person. Within the context of this disclosure, genetic mutations due to exposure to chemicals, specifically, neurotoxins, is addressed.

Many specific chemicals are known to cause genetic mutations given adequate exposure to a person. Such chemicals include ntrosoguanidine (NTG), hdroxyamine NH3OH, base analogs (e.g. BrdU), acids, alylating agents (e.g. N-ethyl-N-nitrosourea (ENU)), methylating agents (e.g. ethyl methanesulfonate (EMS)), polycyclic hydrocarbons (e.g. benzopyrenes found in internal combustion engine exhaust), DNA intercalating agents (e.g. ethidium bromide), oxidative damage caused by oxygen(O)] radicals. One or more of these examples of mutation-causing chemicals may be found in typical commercial and industrial products such as diesel fuel gasoline, aviation gas (AvGas), jet fuel, solvents, paint thinner, alcohol, ethanol, and petroleum refining agents.

Individuals who work closely with these and other neurotoxic chemicals are in danger of exposure to a point that genetic mutation may result. Although many precautions are taken across the board in all industries to protect workers from any exposure, let alone prolonged and harmful exposure, there still exist situations wherein a worker accidentally or minimally encounters exposure to such neurotoxic substances. Further, because of one's genetic makeup and/or history, particular persons may be more susceptible to genetic mutations than others and may even suffer genetic mutation from minimal exposure because of their genetic predisposition.

Thus, an assessment of a person's genetics may lead to a predictable and reliable determination of the person's susceptibility to genetic mutation as a result of exposure to toxic substances typically found in the aviation and refining industries. Such a genetic diagnostic may also be utilized to perform genomic toxicity screening tests to indicate illness or exposure to neurotoxic compounds found in gasoline, diesel, and aviation fuel, among others. Such tests are of particular interest to petrochemical, fuel and refining companies, which assume significant liabilities due to the neurotoxins present in their products and processes. In these and other industries, this genetic diagnostic testing can aid in employee genetic mutation prevention and the promotion of onsite job safety.

Various embodiments and methods of new processes include the assembly and association of genetic material samples with associated genetic mutations, the preparation of microarrays with representative genetic material samples in a pattern best suited for analysis as well as manipulation, and delivery of assimilated and compiled data across a computer network. Various aspects of these embodiments are discussed in FIGS. 1-7 below.

Figure 1:
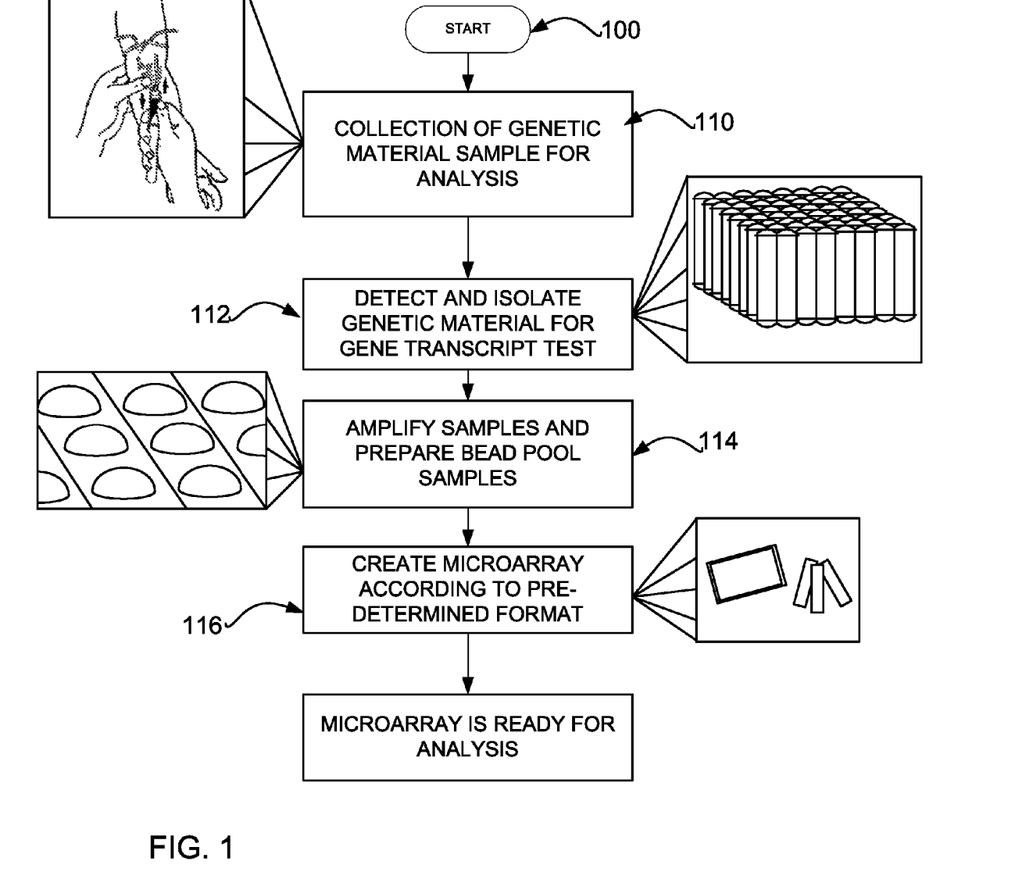
FIG. 1 shows a diagram of a method for preparing a microarray to be used in a broad-based genetic mutation association gene transcript test according to an embodiment of an invention disclosed herein.

FIG. 1 shows a diagram of an overall method 100 for preparing genetic samples that may be used in a broad-based genetic mutation association gene transcript test according to an embodiment of an invention disclosed herein. The method may typically include drawing a blood sample (or obtaining another source of genetic material) from a patient scheduled for genotyping in step 110. Of course, in order to assimilate a broad-based set of data across several genetic mutations, blood samples are typically drawn from several sources. It should be noted that any tissue suitable for gaining access to genetic material (e.g., DNA and/or RNA) may be used, such as liver tissue. Blood cells are easily collected and easily transported making this source for DNA/RNA efficient and effective. The blood sample may typically be collected using a suitable blood collection device such as blood collection tubes that are available from Paxgene™.

The sample is typically properly tagged and labeled by an anonymous yet traceable patient identification. That is, all measures are taken to comply with the Health Insurance Portability and Accountability Act (HIPAA) such that the blood sample is identifiable but also protected from accidental disclosure of privileged information. At the time of collection, additional demographic information may be stored (e.g., written on a tag, stored in a computer database) with the blood sample. Such demographic information may include a number of different patient characteristics and descriptions, such as age, sex, country of origin, race, specific health issues, occupation, birthplace, current living location, etc.

Specific genetic material, such as RNA from the blood sample, may then be detected and isolated in step 112 using an RNA isolation kit such as those that are available from Qiagen™. As mentioned above, RNA isolation may be accomplished at the same physical location as collection or may be accomplished at a remote laboratory after collection. The genetic material isolation process is described in more detail below with respect to FIG. 2.

At step 114, specific sequences in an RNA sample may be amplified using a fluorescence process that may be specific to pre-determined strands of RNA such as available from Illumina™ in a product entitled DASL™. In an alternative embodiment, specific sequences in DNA may also be amplified using a similar fluorescence process that may be specific to pre-determined strands of DNA such as available from Illumina™ in a product entitled Golden Gate™.

The isolation of genetic materials is typically followed by amplification of fluorescently labeled copies that may then be hybridized to specific probes attached to a common substrate, i.e., a microarray. However, the collected and isolated samples may be arranged and analyzed in any manner suitable for analysis. As such, data may be collected and assimilated directly into a computer-based data structure, such as a database, without having to prepare a microarray.

At step 116, the isolated and amplified samples of genetic material may be grouped according to identified sets of strands of genetic material. The groups may be arranged in a specific pattern in bead pools on a microarray according to a predetermined format. Such predetermined formats may include a standard format suitable for individual analysis of all identified genes in isolated RNA/DNA strands. Other predetermined formats may include a side-by-side comparison to one or more control groups of similar genes from control group samples. Other formats may include specific sets of genes suitable for broad-based genetic mutation association, multiple sclerosis association, broad-based diagnostics collection, broad-based predictive treatment data sets, or any other association of genes with samples. Once the microarray has been created in a specific pattern, the emergence of patterns and the like may be ready for analysis at step 118. The preparation of such a microarray is described in more detail in U.S. patent application Ser. No. 11/775,660 entitled, "Method and System for Preparing a Microarray for a Disease Association Gene Transcript Test," assigned to IGD-Intel of Seattle, Wash., which is incorporated by reference. The formats for arranging samples in a microarray typically follow specifics associated with the groupings of blood samples as discussed below with respect to FIG. 2.

Figure 2:
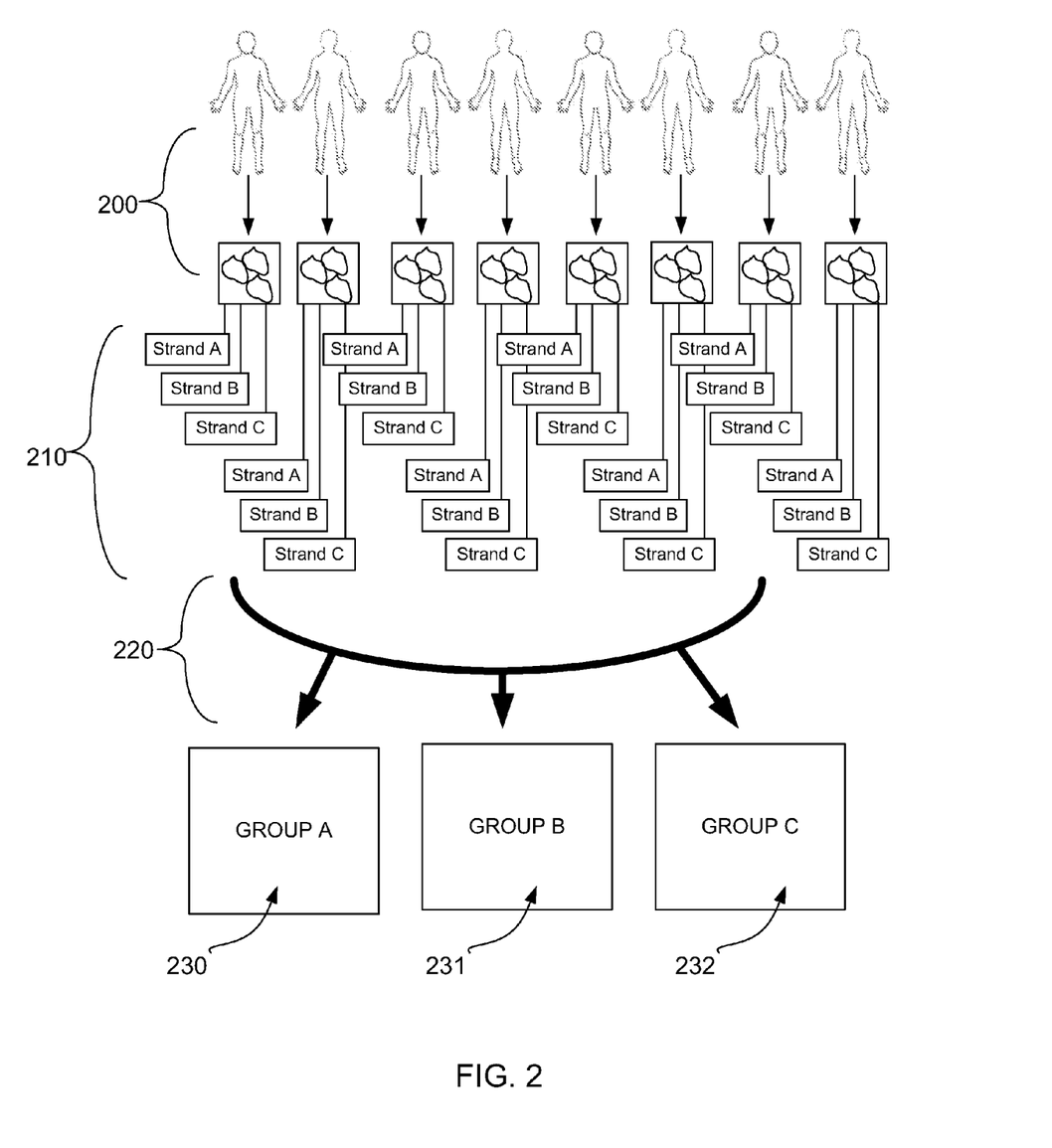
FIG. 2 shows a diagrammatic representation of a method for collecting genetic material samples from several sources and detecting and isolating strands of genetic material for grouping according to an embodiment of an invention disclosed herein.

FIG. 2 shows a diagrammatic representation of a method for collecting blood samples from several sources and identifying strands of genetic material for grouping according to an embodiment of an invention disclosed herein. In an overview of one method disclosed herein, one may begin the method by collecting a plurality of similar blood samples from a plurality of similar sources, the blood samples suitable for genetic material isolation and analysis. Then, identifiable strands of genetic material in each blood sample may be detected and isolated such that the strands of genetic material identifiable by a gene sequence or nucleotide sequence.

Next, for each blood sample, as an identifiable strand emerges, the samples may be separated into sets of samples with similar identifiable strands and then each set of isolated strand samples of genetic materials may be then grouped into groups of genetic material from each of the plurality of blood samples, such that each group comprises similar identifiable strands of genetic material from each blood sample. Once grouped, each group of genetic material maybe associated with a genetic mutation relevant to the identifiable strands comprising each group or any other relevant data that may be useful for diagnostics. Aspects of these broad-based steps are discussed below.

In FIG. 2, several different sources of genetic material may typically be used to obtain several different samples of genetic material. This step is represented in the aggregate at step 200 in FIG. 2 and may be associated with the individual step 110 of FIG. 1. As a result, several different and identifiable samples of genetic material may then be processed to detect and isolate specific genetic material for assimilation into an aggregate context. One such process includes RNA isolation.

Specific gene sequences (i.e., nucleotide sequences) may be identified when detecting and isolating strands of genetic material from each sample at step 210. On an aggregate level, each sample may typically have a first strand, such as STRAND A, such that all gene sequences that may be identified as STRAND A may be isolated and the sample separated from all other strands. Likewise, STRAND B for each sample may be also isolated and its respective sample separated. The case is also the same for STRAND C and every other identifiable strand of genetic material in each sample. Although, only 3 specific strands are shown in FIG. 2, it is well understood in the art that the potential strands that may be isolated number in the thousands.

Such isolation processes may comprise the isolating of genetic material based on strands of RNA as identified by a specific gene sequence as described above. Additionally, the isolation of genetic material may be based upon a gene sequence associated with a gene expression indicative of a specific genetic mutation or even the susceptibility to a specific genetic mutation, a gene sequence associated with a gene expression indicative of a trait, a gene sequence associated with a gene expression indicative of a phenotype, and/or a gene sequence associated with a gene expression indicative of a genotype.

With all strands detected, isolated, and identified, each set of strands (i.e., all samples with STRAND A isolations) across all samples may be grouped together for additional association and analysis at step 220. As such, all expressions of STRAND A may be grouped into GROUP A 230, all expressions of STRAND B may be grouped into GROUP B 231 and all expressions of STRAND C may be grouped into GROUP C 232. Such grouping allows for the assimilation of data on an aggregate level based on various gene expressions as compared to a number of aggregate level aspects of assimilated data. Specifically, demographic information about the source of a sample may be associated with each sample.

Additionally, aggregating information associated with each blood sample may be accomplished through the groupings of similar strands. Such aggregating includes associating a blood sample exhibiting an expression of a gene sequence indicative of a first genetic mutation or susceptibility to the first genetic mutation with the demographic information about the blood sample, associating a blood sample exhibiting an expression of a gene sequence indicative of a first genetic mutation with another blood sample exhibiting an expression of a gene sequence indicative of the first genetic mutation, associating a blood sample exhibiting an expression of a gene sequence indicative of a first genetic mutation with a blood sample exhibiting an expression of a gene sequence indicative of a second genetic mutation, associating a blood sample exhibiting an expression of a gene sequence indicative of a first genetic mutation with a treatment associated with the first genetic mutation, and associating a blood sample exhibiting an expression of a gene sequence indicative of a first genetic mutation with a specific polymorphism.

With any number of associations in place from the groupings, statistical data from the aggregated blood samples based on associations of one blood sample with another may be extrapolated. Such statistical data may include expression rates, inter-related expression rates, etc, of many different genetic mutations.

Application of this unique set of probes will offer a low cost genomic assessment of an individual's state of health through a new and useful clinical diagnostic with regard to genetic mutation and/or a person's susceptibility to specific genetic mutations. Additionally, adding or deleting probes that relate to a given genetic mutation, as new information is presented in peer-reviewed literature may further enhance the benefits of the clinical diagnostic. Adding probe content as information expands is a planned future course of action, as will be appreciated by others in the art. Further yet, the clinical diagnostic may be expanded such that components may be tested as separate, and/or all inclusive tests that address different genetic mutations, job-related concerns, or lifestyle concerns.

Information that may now be gleaned from the groupings of sets of genetic material may be aggregated into in a computer readable medium accessible by a server computer, e.g., a database. Then, such data may be accessed by any connected client computer such that information is provided from the aggregated data to a client computer upon a request from the client computer to the server computer.

Figure 3:
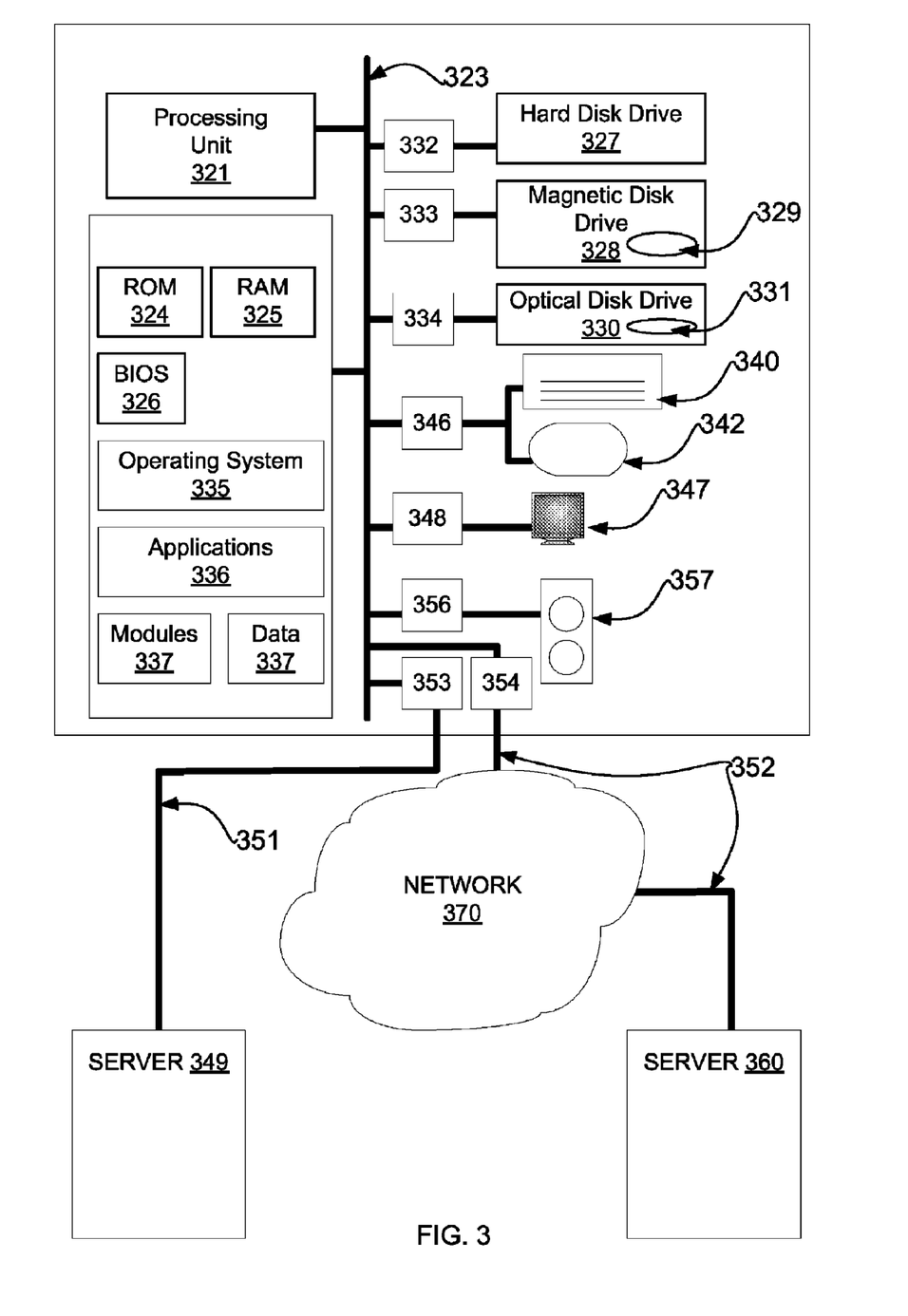
FIG. 3 is a diagrammatic representation of a suitable computing environment in which some aspects of a broad-based genetic mutation association gene-transcript test may be practiced according to an embodiment of an invention disclosed herein.

FIG. 3 is a diagrammatic representation of a suitable computing environment in which some aspects of a broad-based genetic mutation association gene-transcript test may be practiced according to an embodiment of an invention disclosed herein. With reference to FIG. 3, an exemplary system for implementing the invention includes a general purpose computing device in the form of a conventional personal computer 320, including a processing unit 321, a system memory 322, and a system bus 323 that couples various system components including the system memory to the processing unit 321. The system bus 323 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The system memory includes read only memory (ROM) 324 and random access memory (RAM) 325. A basic input/output system (BIOS) 326, containing the basic routines that help to transfer information between elements within the personal computer 320, such as during start-up, is stored in ROM 324. The personal computer 320 further includes a hard disk drive 327 for reading from and writing to a hard disk, not shown, a magnetic disk drive 328 for reading from or writing to a removable magnetic disk 329, and an optical disk drive 330 for reading from or writing to a removable optical disk 331 such as a CD ROM or other optical media. The hard disk drive 327, magnetic disk drive 328, and optical disk drive 330 are connected to the system bus 323 by a hard disk drive interface 332, a magnetic disk drive interface 333, and an optical drive interface 334, respectively. The drives and their associated computer-readable media provide nonvolatile storage of computer readable instructions, data structures, program modules and other data for the personal computer 320. Although the exemplary environment described herein employs a hard disk, a removable magnetic disk 329 and a removable optical disk 331, it should be appreciated by those skilled in the art that other types of computer-readable media which can store data that is accessible by a computer, such as magnetic cassettes, flash memory cards, digital versatile disks, Bernoulli cartridges, random access memories (RAMs), read only memories (ROM), and the like, may also be used in the exemplary operating environment.

A number of program modules may be stored on the hard disk, magnetic disk 329, optical disk 331, ROM 324 or RAM 325, including an operating system 335, one or more application programs 336, other program modules 337, and program data 338. A user may enter commands and information into the personal computer 320 through input devices such as a keyboard 340 and pointing device 342. Other input devices (not shown) may include a microphone, joystick, game pad, satellite dish, scanner, or the like. These and other input devices are often connected to the processing unit 321 through a serial port interface 346 that is coupled to the system bus, but may be connected by other interfaces, such as a parallel port, game port or a universal serial bus (USB). A monitor 347 or other type of display device is also connected to the system bus 323 via an interface, such as a video adapter 348. One or more speakers 357 are also connected to the system bus 323 via an interface, such as an audio adapter 356. In addition to the monitor and speakers, personal computers typically include other peripheral output devices (not shown), such as printers.

The personal computer 320 operates in a networked environment using logical connections to one or more remote computers, such as remote computers 349 and 360. Each remote computer 349 or 360 may be another personal computer, a server, a router, a network PC, a peer device or other common network node, and typically includes many or all of the elements described above relative to the personal computer 320, although only a memory storage device 350 or 361 has been illustrated in FIG. 3. The logical connections depicted in FIG. 3 include a local area network (LAN) 351 and a wide area network (WAN) 352. Such networking environments are commonplace in offices, enterprise-wide computer networks, intranets and the Internet. As depicted in FIG. 3, the remote computer 360 communicates with the personal computer 320 via the local area network 351. The remote computer 349 communicates with the personal computer 320 via the wide area network 352.

When used in a LAN networking environment, the personal computer 320 is connected to the local network 351 through a network interface or adapter 353. When used in a WAN networking environment, the personal computer 320 typically includes a modem 354 or other means for establishing communications over the wide area network 352, such as the Internet. The modem 354, which may be internal or external, is connected to the system bus 323 via the serial port interface 346. In a networked environment, program modules depicted relative to the personal computer 320, or portions thereof, may be stored in the remote memory storage device. It will be appreciated that the network connections shown are exemplary and other means of establishing a communications link between the computers may be used.

Figure 4:
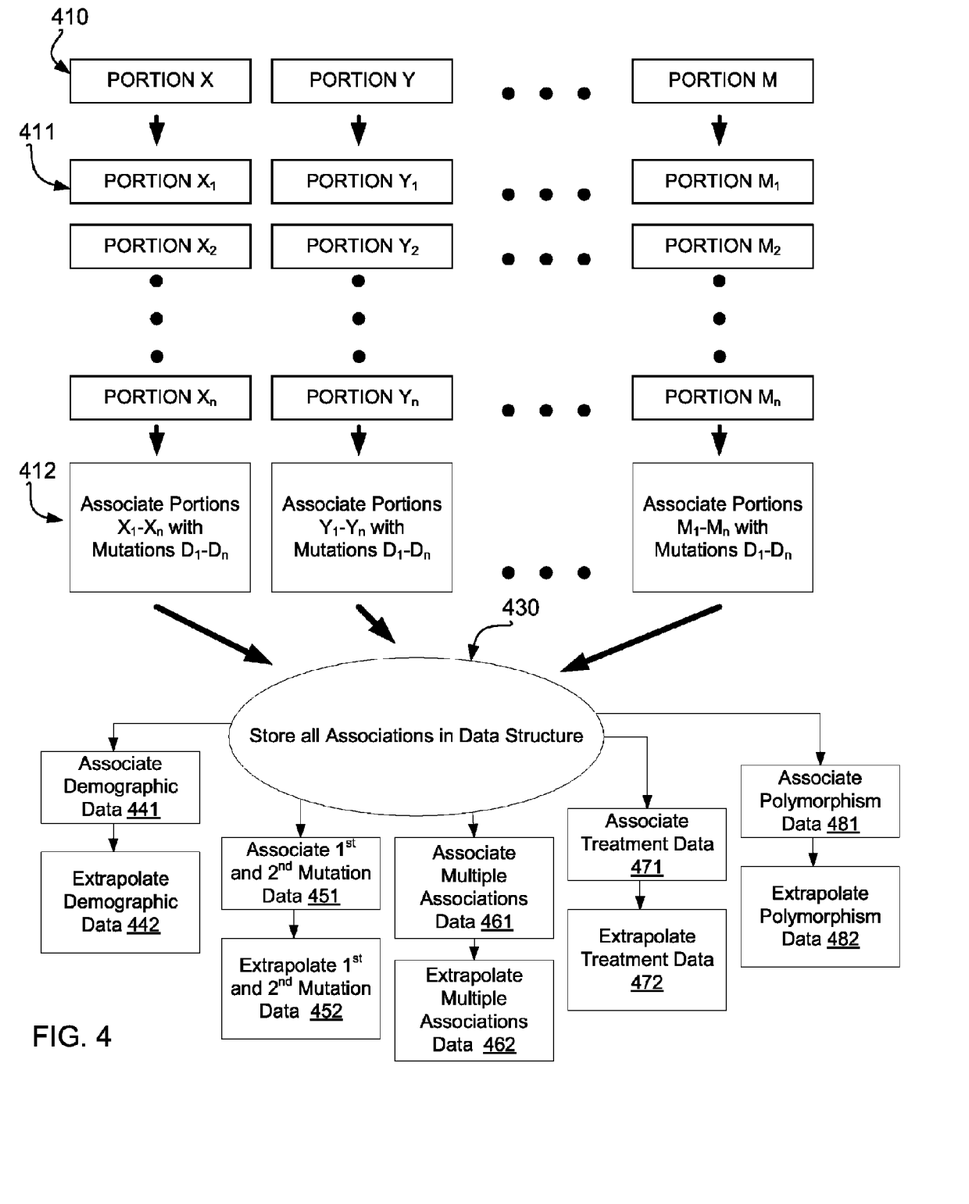
FIG. 4 is a diagrammatic representation of a system and method for establishing a data structure to be used in a broad-based genetic mutation association gene transcript test according to an embodiment of an invention disclosed herein.

FIG. 4 is a diagrammatic representation of a system and method for establishing a data structure to be used in a broad-based genetic mutation association gene transcript test according to an embodiment of an invention disclosed herein.

As samples of genetic material from various sources are gathered, each sample may be identified uniquely by the source of the sample. For example, amongst all samples in FIG. 4, (i.e., Sample X through Sample M), each sample 410 may be identified uniquely by a tracking identification. For the purposes of the eventual data structure, the first sample may be Sample X, the next may be Sample Y, and so on all the way to the last sample, Sample M. It is understood that these samples 410 may be arranged according to some specific method as described above with respect to FIG. 2 and/or may also be disposed on a microarray prepared especially for a method and system described herein.

Once all samples 410 are uniquely identified by source, each sample may be further subdivided into specific portions 411 wherein a specific portion may exhibit a specific genetic expression as described above. As used herein, a portion 411 refers to any amount of a genetic material sample that exhibits a specific genetic expression. Portion does not, in any manner, denote a specific amount or quantity of genetic material. As such, each sample may have a very large number of portions, such that each one exhibits a specific genetic expression.

In assembling a data structure, each portion 411 may be further identified as exhibiting one specific gene expression (or not expressing the gene, as the case may be). Thus, Portion $X_1$ may be identified as having a first specific nucleotide sequence, Portion $X_2$ may be identified as having a second specific nucleotide sequence and so on until the last portion is identified as having an nth specific nucleotide sequence. With the identification of each portion as containing one of $1^{st}$-$n^{th}$ specific nucleotide sequences, the association of the portions with the source (i.e., Sample X) is maintained. A similar portioning of Samples Y through M also maintains the specific association with the source sample. That is, Sample Y is portioned into portion $Y_1$ through $Y_n$ each uniquely exhibiting the specific $1^{st}$ through $n^{th}$ nucleotide sequence respectively. This portioning and association process occurs for all samples through the $M^{th}$ sample.

Next, at aggregate step 412, each portion is associated with a respective genetic mutation. That is portion $X_1$-$X_n$ is associated with genetic mutation $D_1$-$D_n$ such that each genetic mutation that is associated with each portion corresponds uniquely with the specific nucleotide sequence exhibited by the portion. Similarly, portions $Y_1$-$Y_n$ are associated with genetic mutations $D_1$-$D_n$ all the way through the $M^{th}$ set of portions wherein portions $M_1$-$M_n$ are associated with genetic mutations $D_1$-$D_n$, respectively.

With each portion of each sample associated with a specific genetic mutation, all broad-based genetic mutation association gene transcript data may be stored in a single data structure 430. With such a data structure 430 in place a number of different associations and data trends may be extrapolated.

For example, if demographics data about the source of the sample was collected at the same time that the sample was collected, the demographics data may also be associated with the expression of specific genetic mutations by associating the demographics data with the portions of each sample exhibiting an expression for such a genetic mutation. Then, with these data associations in place within the data structure, such associative data may be extrapolated that encompasses a first genetic mutation associated with a portion of a sample with the demographic information about the source of the sample. In the aggregate, specific trends about demographic data and specific genetic mutations may be garnered.

As another example, additional trend data may be garnered by associating a portion of a sample from a first source exhibiting the specific gene expression indicative of a first genetic mutation with a portion of a sample from the first source exhibiting the specific gene expression indicative of a second genetic mutation. Then, with these associations in place additional trend data may be garnered by extrapolating associative data encompassing a portion of a sample from a first source exhibiting the specific gene expression indicative of a first genetic mutation with a portion of a sample from the first source exhibiting the specific gene expression indicative of a second genetic mutation. Similarly, such trend data may be garnered by associating specific polymorphisms with specific portions exhibiting such nucleotide sequences associated with the polymorphisms.

Additional information about multiple genetic mutation associations may be garnered by associating the portions from the first sample respectively exhibiting specific gene expressions associated with the first and second genetic mutation with a portion of a sample from a second source exhibiting the specific gene expressions associated with either the first or the second genetic mutation. With these associations, one may extrapolate associative data regarding a portion of a sample from a first source exhibiting the specific gene expression indicative of a first genetic mutation, a portion of a sample from the first source exhibiting the specific gene expression indicative of a second genetic mutation, and a portion of a sample from a second source exhibiting the specific gene expressions associated with either the first or the second genetic mutation in an effort to yield additional trend data.

As yet another example, treatment data may be expressed by associating a portion of a sample from a first source exhibiting the specific gene expression indicative of a first genetic mutation with a treatment linked to the first genetic mutation. Further, such treatment data may also be extrapolated from such associative that encompasses a portion of a sample from a first source exhibiting the specific gene expression indicative of a first genetic mutation with a treatment linked to the first genetic mutation.

Figure 5:
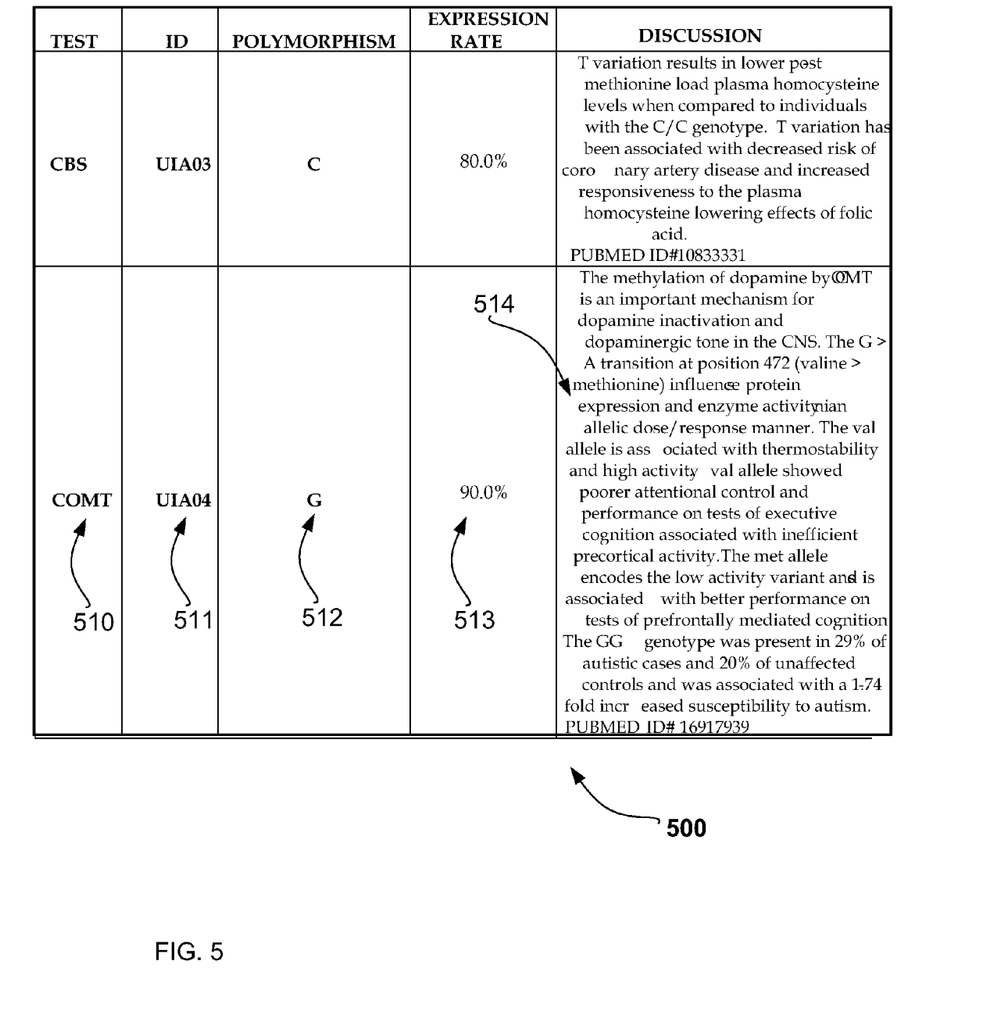
FIG. 5 shows a typical arrangement of data that may be associated in a database of information derived from a broad-based genetic mutation association gene transcript test according to an embodiment of an invention disclosed herein.

FIG. 5 shows a typical arrangement of data that may be associated in a database of information derived from a broad-based genetic mutation association gene transcript test according to an embodiment of an invention disclosed herein. The data associated with the portions of genetic material stemming from traceable samples may be arranged in a data structure 500 according to FIG. 5. In FIG. 5, the data structure may associate a specific test 510, an ID 511, a polymorphism 512, an expression rate 513, and a discussion 514.

The specific test 510 may typically comprise a known set of nucleotide sequences in which one should examine to determine the presence or non-existence of specific genetic mutation or susceptibility to such a genetic mutation or genetic disorder. Based on the polymorphism 512, and ratio 513, the interpretation/discussion 514 will indicate the possibilities for diagnosis, or suggest treatment for a specific exposure.

The ID 511 may typically comprise the specific nucleotide sequence know to be associated with the test and/or genetic mutation associated collectively.

The Polymorphism 512 may typically refer to the specific nucleotide that is anomalous when a genetic mutation is expressed. That is, in the specific nucleotide sequence identified in the ID 511, one (or more) of the nucleotide express a polymorphism as identified in this data store.

The expression rate 513 may typically comprise a rate of expression of the polymorphism either as a function of the data set within the data structure or as an expression of the rate of a larger population.

Finally, the data structure may also include a discussion 514 that is obtained from clinically relevant understanding from sources of peer reviewed literature and published clinical studies.

With at least some of these data sets in a data structure, a broad-based genetic mutation association gene transcript test data structure may be realized. Such a data structure may be characterized by a first tangible (i.e., fixed in some tangible medium) data set operable to store a gene expression isolated from genetic material from a specific source, the gene expression associated with a first genetic mutation, a second tangible data set operable to store an identification of the source and associated with the first tangible data set, a third data set associated with a specific toxic substance linked to the first genetic mutation and a fourth tangible data set operable to store at least one other association with a second genetic mutation, the second genetic mutation associated with a second gene expression.

Additional data sets may include a fifth tangible data set operable to store an identification of a specific test associated with the first genetic mutation, a sixth tangible data set operable to store an expression rate associated with the first genetic mutation and associated with the first gene expression, and a seventh tangible data set operable to store a discussion associated with the first genetic mutation and associated with the first gene expression. Such a data structure may be realized in a fixed computer-readable medium, such as a database, or may be fixed to another medium such as a substrate hosting a microarray of genetic samples.

A specific combination of nucleic acid sequences taken from isolated regions of the human genome may be reflected as custom content on a platform independent gene expression microarray. A complete list of nucleic acid sequences form the elements analyzed within this human genome examination may form the basic nature of a gene transcript test, which is typically intended for clinical use in effectively detecting transcribed alterations in the genetic code that have a documented relationship with one or more genetic mutations, association with therapeutic response, and/or treatment for one or more genetic mutations. The content of the test may assess RNA through quantitative (measurement and assessment of transcript present within the tissue) and qualitative (measurement of genomic regions) means.

This nucleic acid array may be comprised of probe sequences isolated to detect regions within a given gene that most effectively indicate expression levels and that represent polymorphic sections indicating which sequence from the genome an individual is actually expressing. The nucleic acid sequences deemed present in the amplified portions of a sample isolated from standard blood draw and/or genetically mutated tissue, may be detected by hybridizing the amplified portions to the array and analyzing a hybridization pattern resulting from the hybridization.

Association of test results with claims and assessments of clinical relevance may be assimilated and documented as conclusions formed through a comprehensive compilation of peer-reviewed literature (or other periodic update). Ongoing modifications to these claims and assessments may be performed through quarterly protocol assessment and maintenance of a peer-to-peer physician support network supported through existing and impending corporate associations.

Paper reporting of the test results may indicate the outcome from a subset of 1 to 50 genetic sequences. Additional reporting for several other sequences may be made available through alternative measures. These measures may enable physicians to access their patient's information relative to all other patients having ordered the test through a variety of associative clustering methods (hierarchical, divisive, and associative). The concept of creating real-time genotype/phenotype association accessible to physician-to-physician networks may be further promoted as a desired goal. Physicians will be able to analyze their own patient's data relative to all other data existing individuals who have had the test performed.

Examples of polymorphisms assessed may be single nucleotide polymorphisms (SNPs), deletions, and/or deletion insertion sequences. Further, the polymorphisms predicted to be present in the amplified portions may already be determined. Further yet, the nucleic acid sample may be genomic DNA, cDNA, cRNA, RNA, total RNA or mRNA. With these variations, the SNP, deletion, or insertion may be associated with a genetic mutation, the efficacy of a drug, and/or associated with predisposition towards/against development of aforementioned ailment(s). Typically, output data may be packaged in a computer-readable medium (e.g., a CD or DVD) and delivered to a customer, such as a subscribing physician.

Figure 6:
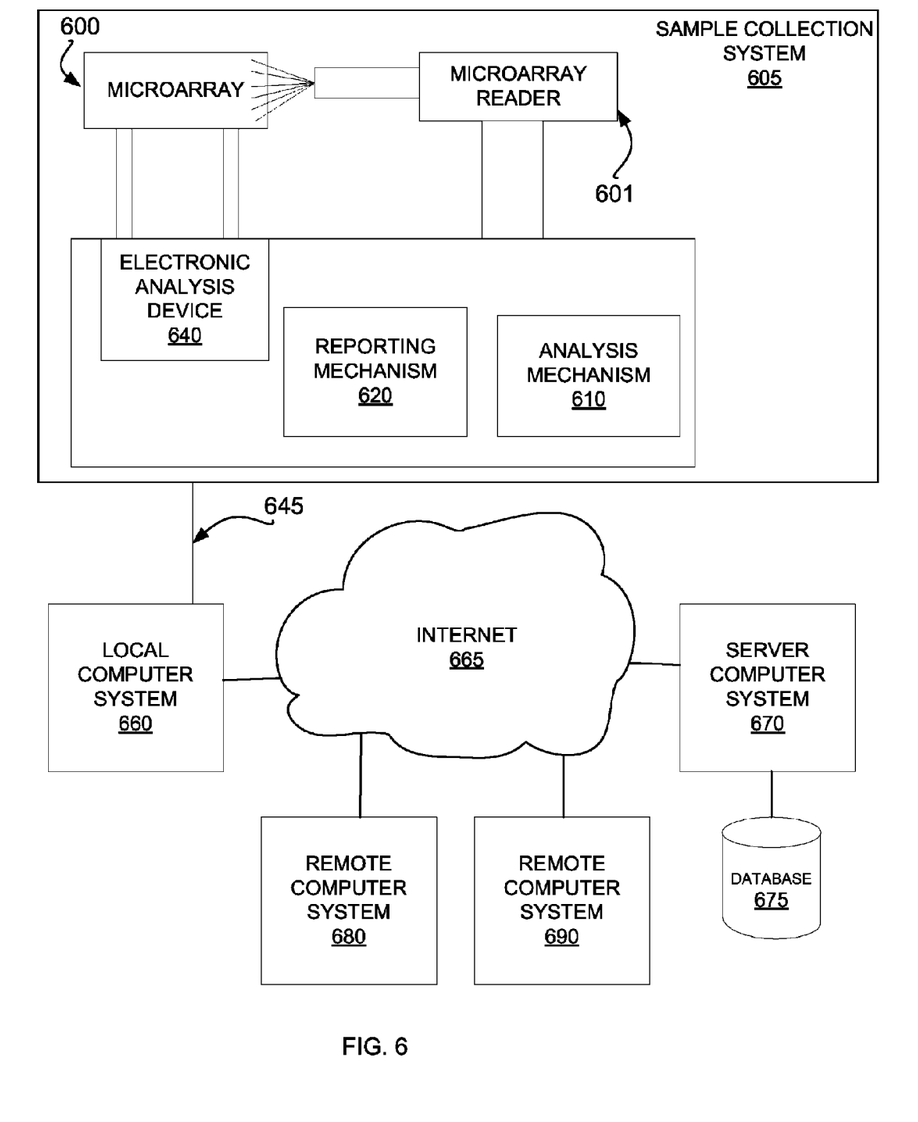
FIG. 6 shows a diagrammatic representation of a method and system for establishing a broad-based genetic mutation association gene transcript test according to an embodiment of an invention disclosed herein.

FIG. 6 shows a diagrammatic representation of a method and system for establishing a broad-based genetic mutation association gene transcript test according to an embodiment of an invention disclosed herein. In this embodiment, a microarray 600 may be characterized by an arrangement of different identified gene expressions based upon an association with many different samples and many different sample sources. Several other arrangements of data exist as other embodiments as well. As such, depending on the known arrangement of samples, specific patterns of the presence of phenotypes or lack thereof determine the type of information to be garnered from each prepared microarray 600. As a result of this embodiment, specific patterns emerge indicating a likelihood of occurrence of a SNPs, insertions, or deletions in various regions.

Such patterns may be read by a microarray reader 601. The microarray reading device typically includes a microarray station 602 operable to view a microarray 600. As briefly discussed above, a typical microarray 600 will include a plurality of deposit wells suitable for hosting samples of genetic material. The wells disposed on a substrate may be arranged such that each row is suited for hybridizing a genetic material sample such that a unique gene expression may be identified (i.e., one gene per row). Further, each column is suited for having each sample in each row in the column be associated with a single source of genetic material (i.e., one person per column).

The microarray reader 601 may also typically include an analysis mechanism 610 operable to analyze a pattern displayed on the microarray 600 and a reporting mechanism 620 operable to deliver a report of the analysis. The microarray reader 601 may also have an electronic microarray assessment apparatus 640 operable to determine a pattern of gene expression from a series of electrical pulses sent to and received from the stationed microarray 600.

Microarrays 600 are quite useful is mapping or "expressing" data about the makeup of the genetic material disposed thereon. Applications of these microarrays 600 include the following. Messenger RNA or Gene Expression Profiling— monitoring expression levels for thousands of genes simultaneously is relevant to many areas of biology and medicine, such as studying treatments, mutations, and developmental stages. For example, microarrays 600 can be used to identify diseased genes or mutated genes by comparing gene expression in non-mutated and normal cells. Other uses for microarrays 600 are known and/or contemplated but not discussed herein for brevity.

With such a microarray 600 available for analysis and coupled with multiple additional prepared microarrays, broad-based data about the occurrence or absence of genetic mutations and/or specific gene sequences begins to emerge. The microarray 600 may be scanned and intensity data extracted to associate presence/absence of genetic material in the original sample. This data may be assimilated in a large database of information together with additional information such as diagnosis and treatment information, to provide a multitude of information about a large number of data sets. As the data is assimilated, a comprehensive literature search offering substantiated associations of genetic mutation with gene sequence alterations may be provided. The data are rendered anonymous and uploaded into a central repository that allows cross-sample comparison and ultimately, earlier detection of genetic mutation.

Figure 7:
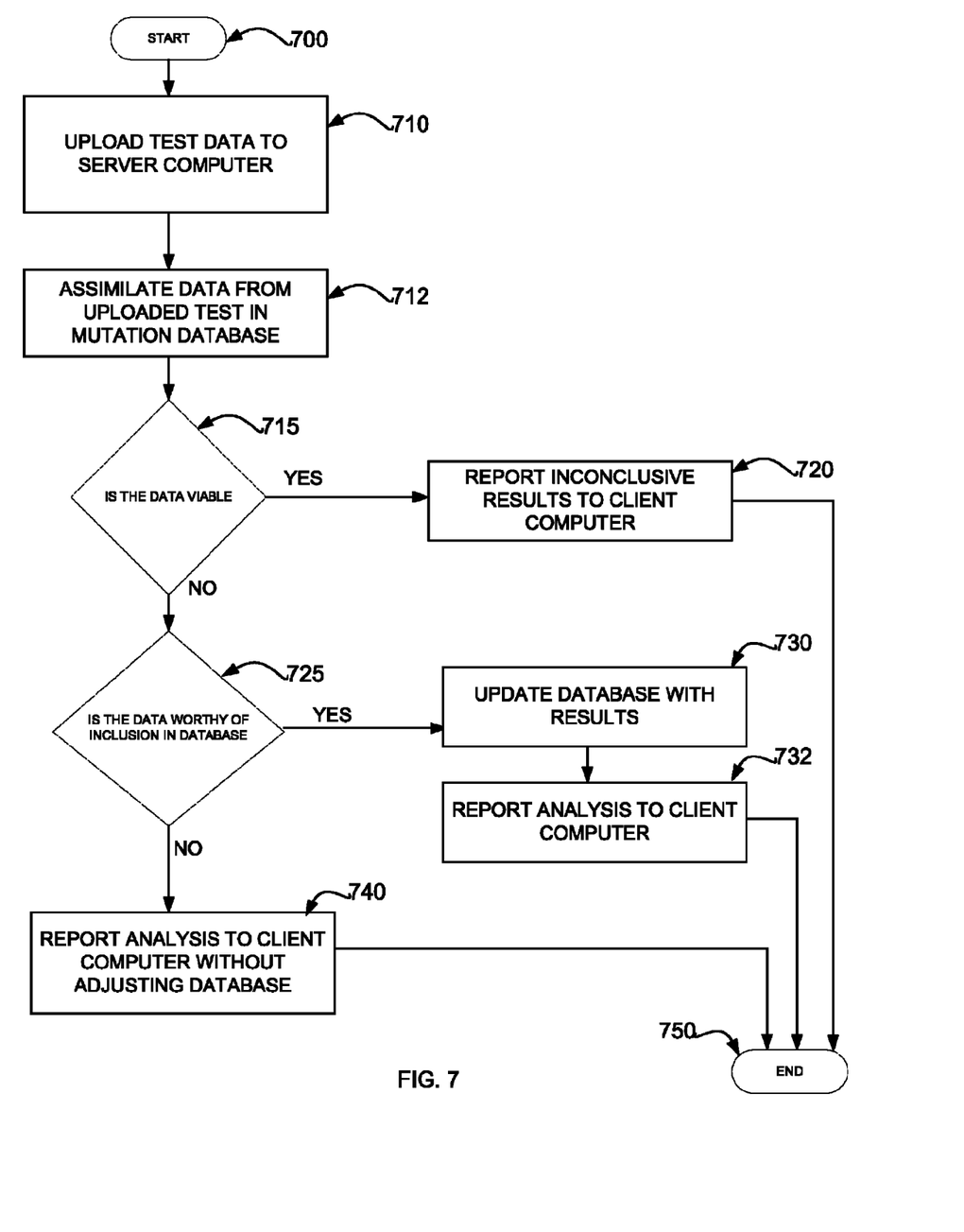
FIG. 7 is a flow chart of a method for diagnosing and/or screening a patient for potential genetic effects of exposure to a neurotoxic substance according to an embodiment of an invention disclosed herein.

FIG. 7 is a flow chart of a method for diagnosing and/or screening a patient for potential genetic effects of exposure to a neurotoxic substance according to an embodiment of an invention disclosed herein. The method depicted here in FIG. 7 presumes that genetic samples from at least one source has been collected and prepared for assimilation. As such in an overview of one computer-related method and/or computer executable instructions fixed in a computer-readable medium depicted in FIG. 7, one may collect genealogical data about a person and store the collected data in a data set at a client computer, wherein the genealogical data includes a plurality of genetic sequences. Then, the data set may be transmitted to a server computer that is communicatively coupled to the client computer. The server computer may assess the data set to determine an assessment of at least one genetic sequence that is associated with a specific genetic mutation caused by exposure to a toxic substance. Once assessed, the server computer may return the assessment to the client computer.

Thus, a step 710, the assimilated genealogical test data may be transmitted (i.e., uploaded) to a server computer that hosts various database and analysis programs for a broad-based genetic mutation association gene transcript test. The genealogical data may be collected from an analysis of a microarray that includes genetic material samples from the person. The data set may have specific association embedded therein in including associations between the genealogical data and information about the source of the genealogical data as well as associations between specific isolations of the genealogical data and a corresponding genetic mutation.

At step 712, the uploaded test data may be assimilated into a database of aggregately associated mutation analysis data. At step 715, the server computer may analyze the uploaded data to determine if the data is valid. Valid data may be verified by a statistical analysis of the data presented. Results that fall outside of one or two standard deviations from all previously assimilated data may be deemed to be invalid. Invalid data may be discarded and not assimilated into the database. Invalid results may then be reported to the client at step 720.

If, however, the data sets are determined to be valid, a second assessment of the data sets occurs at step 725. Thus, the data set is assessed as to its worthiness for inclusion in the database. If the data is duplicative of other data already assimilated, then no need exists for its inclusion. Further, if all relevant associations and conclusion based on an analysis yields no new information, again, the data may simply be discarded without assimilation into the database. An analysis is reported to the client without assimilating the data at step 740. If the data is particularly useful, the database may be updated at step 730 and the client notified at step 732. The method of FIG. 7 ends at step 750.

Further, as the database is updated with valid and worthy data, other connected client computers may also be notified of the changes to the database. This allows for other physicians to see new results and likewise review such results for use with their own patients and diagnostics. Further yet, the entire method described above may also be applied in the context of assessing a person's susceptibility to genetic mutations based upon exposure to toxic substances.

While the subject matter discussed herein is susceptible to various modifications and alternative constructions, certain illustrated embodiments thereof are shown in the drawings and have been described above in detail. It should be understood, however, that there is no intention to limit the claims to the specific forms disclosed, but on the contrary, the intention is to cover all modifications, alternative constructions, and equivalents falling within the spirit and scope of the claims.

What is claimed is:

1. A computer-related method, comprising:
   collecting genetic data about a person and storing the collected data in a data set at a client computer, the genetic data including a plurality of genetic sequences;
   transmitting the data set to a server computer that is communicatively coupled to the client computer;
   assessing the data set to determine an assessment of at least one genetic sequence that is associated with a specific genetic mutation caused by exposure to a toxic substance; and
   returning the assessment to the client computer.

2. The computer-related method of claim 1 wherein the genetic data is collected from an analysis of a microarray that includes genetic material samples from the person.

3. The computer-related method of claim 1 wherein the collecting the genetic data into the data set further comprises:
   associating the genetic data with information about the source of the genetic data; and
   associating specific isolations of the genetic data with a corresponding genetic mutation.

4. The computer-related method of claim 1 wherein assessing the data set further comprises:
   comparing the data set to a database of information assembled from many other data sets that are stored in a database;
   identifying specific genetic sequences in the transmitted data set that includes a genetic mutation caused by exposure to a toxic substance; and
   identifying specific genetic sequences in the transmitted data set that corresponds to susceptibility to a genetic mutation caused by exposure to a toxic substance.

5. The computer-related method of claim 4 wherein assessing the data set further comprises:
   identifying a specific genetic sequence in the transmitted data set that includes a second genetic mutation caused by exposure to a second toxic substance; and
   determining a rate of correlation between identified genetic sequences.

6. The computer-related method of claim 4, further comprising:
   determining if the data from the transmitted data set is valid; and
   updating the database with the newly transmitted data set.

7. The computer-related method of claim 6 further comprising:
   notifying the client computer that the data set is valid; and
   notifying the client computer that the database is updated with the transmitted data set.

8. The computer-related method of claim 6 further comprising notifying at least one other client computer that the database has been updated with a new data set.

9. A system for assessing genetic data for susceptibility to genetic mutations from exposure to a toxic substance, the system comprising:
   a client computer operable to store collected genetic data about a person in a data set in a data store, the collected genetic data including a plurality of genetic sequences;
   a data transmission device coupled to the client computer and operable to transmit the data set to a server computer that is communicatively coupled to the client computer;
   an assessment program module executing at the server computer, the assessment program operable to assess the data set to determine an assessment of at least one genetic sequence that is associated with a specific genetic mutation caused by exposure to a toxic substance; and
   a reporting program module executing at the server computer, the reporting program operable to return the assessment to the client computer.

10. The system of claim 9, further comprising a validation program module executing on the server computer, the validation program module operable to determine if the newly generated assessment based upon the transmitted data set is valid.

11. The system of claim 10, further comprising an update program module executing on the server computer, the update program module operable to update a database of assessments with the newly generated assessment based upon the transmitted data set if the data set is determined to be valid.

12. The system of claim 11, further comprising reporting program module executing on the server computer, the reporting program module operable to report a valid update to the database to a plurality of other communicatively coupled client computers.

13. The system of claim 9, further comprising a sample collection system operable to collect genetic data by analyzing a microarray of genetic material, the sample collection system coupled to the client computer.

14. A non-transitory computer-readable medium having computer-executable instructions operable for:
receiving a data set of genetic data about a person, the genetic data including a plurality of genetic sequences,
storing the genetic data set in a data store of other genetic data sets;
assessing the received genetic data set to determine an assessment of at least one genetic sequence that is includes a specific genetic mutation caused by exposure to a toxic substance; and
transmitting the assessment to a communicatively coupled client computer.

15. The computer-readable medium of claim 14 having further executable instructions for associating a first genetic sequence known to be linked to a first genetic mutation with a second genetic sequence known to be linked to a second genetic mutation.

16. The computer-readable medium of claim 14 having further executable instructions for determining a likelihood of developing a specific genetic mutation based upon the assessment of the transmitted genetic data.

17. The computer-readable medium of claim 14 having further executable instructions for identifying a dormant genetic mutation based upon the assessment of the transmitted genetic data.

18. The computer-readable medium of claim 14 having further executable instructions for determining a rate of occurrence of a specific genetic mutation based upon the assessment of the transmitted genetic data.

19. The computer-readable medium of claim 14 having further executable instructions for determining risk factors for a specific genetic mutation based upon the assessment of the transmitted genetic data.

* * * * *